United States Patent [19]

Watanabe et al.

[11] Patent Number: 5,050,608
[45] Date of Patent: Sep. 24, 1991

[54] SYSTEM FOR INDICATING A POSITION TO BE OPERATED IN A PATIENT'S BODY

[75] Inventors: Eiju Watanabe, Tokyo; Shinya Manaka, Kanagawa; Yukio Kosugi, Tokyo, all of Japan

[73] Assignee: Medirand, Inc., Tokyo, Japan

[21] Appl. No.: 577,068

[22] Filed: Sep. 4, 1990

Related U.S. Application Data

[63] Continuation of Ser. No. 217,836, Jul. 12, 1988, abandoned.

[51] Int. Cl.$^5$ ............................................. A61B 19/00
[52] U.S. Cl. ................................ 128/653 R; 606/130; 378/20; 378/205
[58] Field of Search ............... 128/653, 782; 606/130; 378/4, 8, 20, 99, 205

[56] References Cited

U.S. PATENT DOCUMENTS

| | | | |
|---|---|---|---|
| 4,571,834 | 2/1986 | Fraser et al. | 128/782 |
| 4,638,798 | 1/1987 | Shelden et al. | 128/303 B |
| 4,750,487 | 6/1988 | Zanetti | 128/303 B |
| 4,791,934 | 12/1988 | Brunnett | 128/303 B |

FOREIGN PATENT DOCUMENTS 2094590 9/1982 United Kingdom ............ 128/303 B

Primary Examiner—William E. Kamm
Assistant Examiner—Scott R. Akers

[57] ABSTRACT

An articulated arm has a plurality of arms connected to each other by joints. A pointer is connected to one of the plurality of arms. The arm nearest the pointer is the foremost arm of the articulated arm. Angular displacement sensors are provided at joints of the articulated arm, for producing angular signals. Tomographical images of a patient's body are displayed on a cathode-ray tube. The angular signals are converted to tomographical position signals corresponding to the tomographical images on the cathode-ray tube. In response to the tomographical position signals, the position of the tip of the pointer is displayed on the cathode-ray tube with a mark. The system can be used, for example, in locating a position on a patient's body where an operation is to be performed.

9 Claims, 4 Drawing Sheets

SYSTEM FOR INDICATING A POSITION TO BE OPERATED IN A PATIENT'S BODY

This application is a continuation of application Ser. No. 07/217,836 filed on July 12, 1988, now abandoned.

BACKGROUND OF THE INVENTION

The present invention relates to an on-line guidance system for guiding to a position on a patient's body, where an operation will be performed. One particular use of the guidance system is to display a position in a patient's brain where an operation should be performed. The display is made, for example, on a cathode-ray tube.

Recent developments in diagnostic procedures in neurosurgery enable the exact position of an affected part to be displayed by an MRI (magnetic resonance imaging) or CT (computer tomography) technology.

One problem in neurosurgical operations involves difficulty in finding out the exact positions of neoplasmas which are shown on tomographical images.

During an on-going neurosurgical procedure, even for well trained neurosurgeons, it is time-consuming work to find the exact position in the brain that corresponds to the MRI or CT images. Also, there is a problem that damage to normal tissues can occur during uncertain searching procedures.

SUMMARY OF THE INVENTION

The object of the present invention is to provide a system which may exactly lead to a position where an operation should be performed. This is done with tomographical images displayed on a cathode-ray tube.

According to the present invention, there is provided a system for indicating a position in a patient's body where an operation is to be performed. The system includes articulated (jointed) arm having a plurality of arms (jointed) articulated with each other, and a pointer provided on an end of a foremost arm, that is, the arm next to the pointer. Angular displacement sensors are provided at joints of the articulated arm. The sensors for producing an angular signal representing an angular displacement of a forward side of the arm. A cathode-ray tube displays tomographical images of a patient's body and there are means responsive to angular signals for producing arm position signals representing position of a tip of the pointer. Conversion means are used for converting the arm position signals to tomographical position signals corresponding to the tomographical images on the cathode-ray tube. There are also means responsive to the tomographical position signals for producing a video signal for displaying the position of the tip of the pointer on the cathode-ray tube with a mark.

In an aspect of the invention, the pointer is structured to be axially retracted.

These and other objects and features of the present invention will become more apparent from the following detailed description with reference to the accompanying drawings.

DETAILED DESCRIPTION OF THE PREFERRED EMBODIMENT

Figure 1:
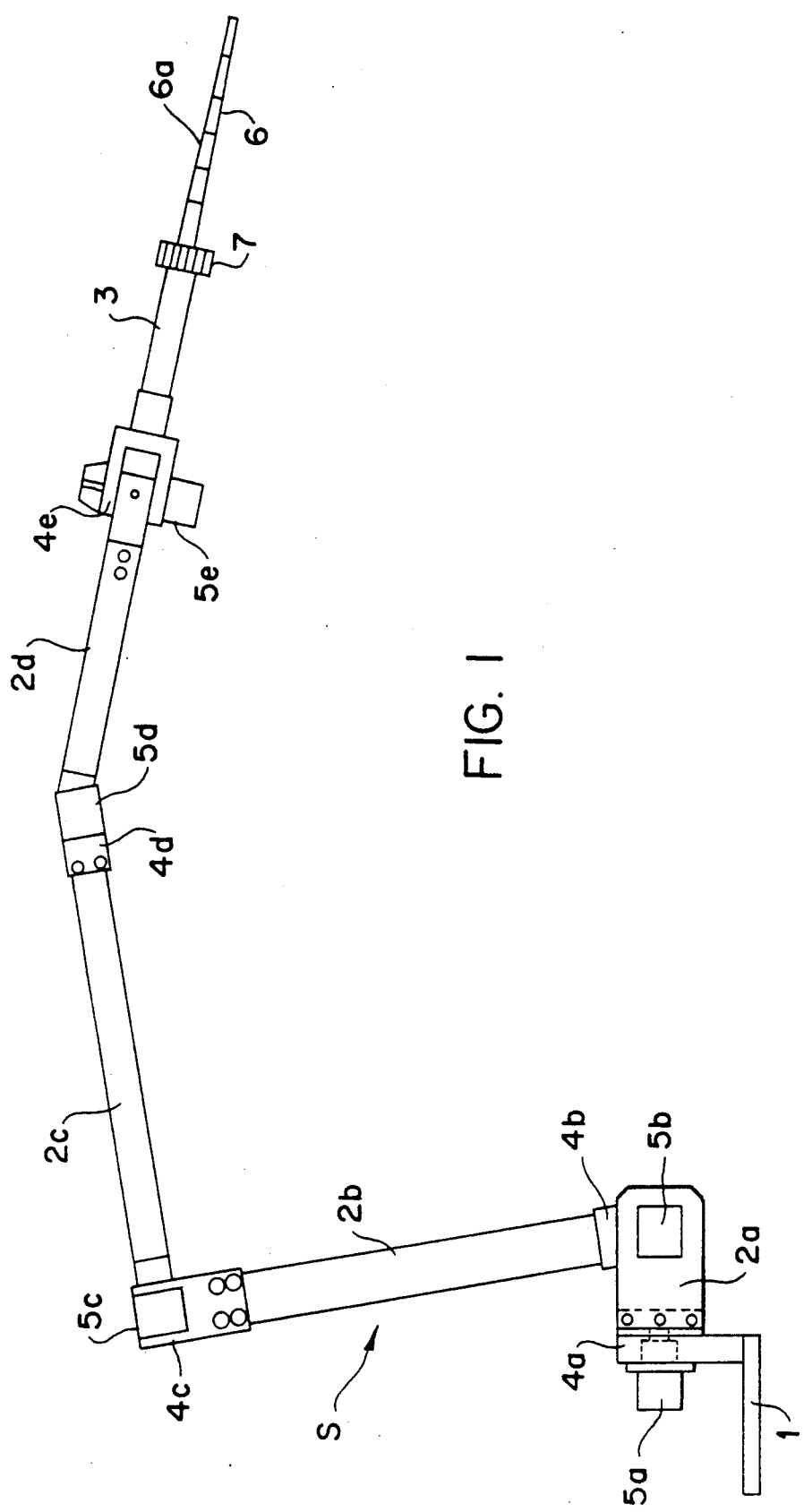
FIG. 1 is a side view of an articulated arm.
Figure 2:
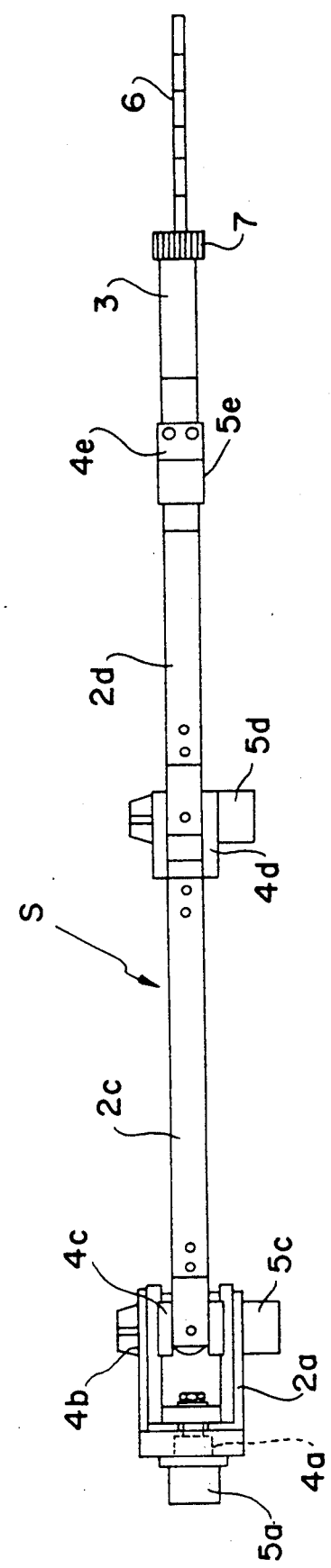
FIG. 2 is a plan view of the articulated arm.

Referring to FIGS. 1 and 2, an articulated arm S comprises an L-shaped base 1, first arm 2a, second arm 2b, third arm 2c, fourth arm 2d, end cylindrical holder 3, and pointer 6. The first arm 2a has a bifurcated end and is pivotally mounted on a horizontal shaft 4a secured to the base 1. The second arm 2b is articulated with the first arm 2a at the bifurcated end by a joint 4b which is perpendicular to shaft 4a. Similarly, third arm 2c is articulated with the second arm 2b by a joint 4c, and third and fourth arms 2c and 2d are articulated with each other by a joint 4d. The holder 3 is articulated with the fourth arm 2d by a joint 4e a shaft of which is perpendicular to the shaft of the joint 4d. Thus, the pointer 6 can be universally moved.

At joints 4a, 4b, 4c, 4d, and 4e, 5a, 5b, 5c, 5d and 5e are provided, each of which is provided to produce a digital output signal representing an angular displacement of a forward side arm, respectively. The pointer 6 is slidably mounted in the holder 3 and has a plurality of click notches 6a serving as calibrations. Each of the notches 6a is structured to engage a spring loaded notch (not shown) provided in the holder so as to be positioned at the notch. The pointer 6 can to be secured to the holder 3 by a nut 7, for example.

Figure 3:
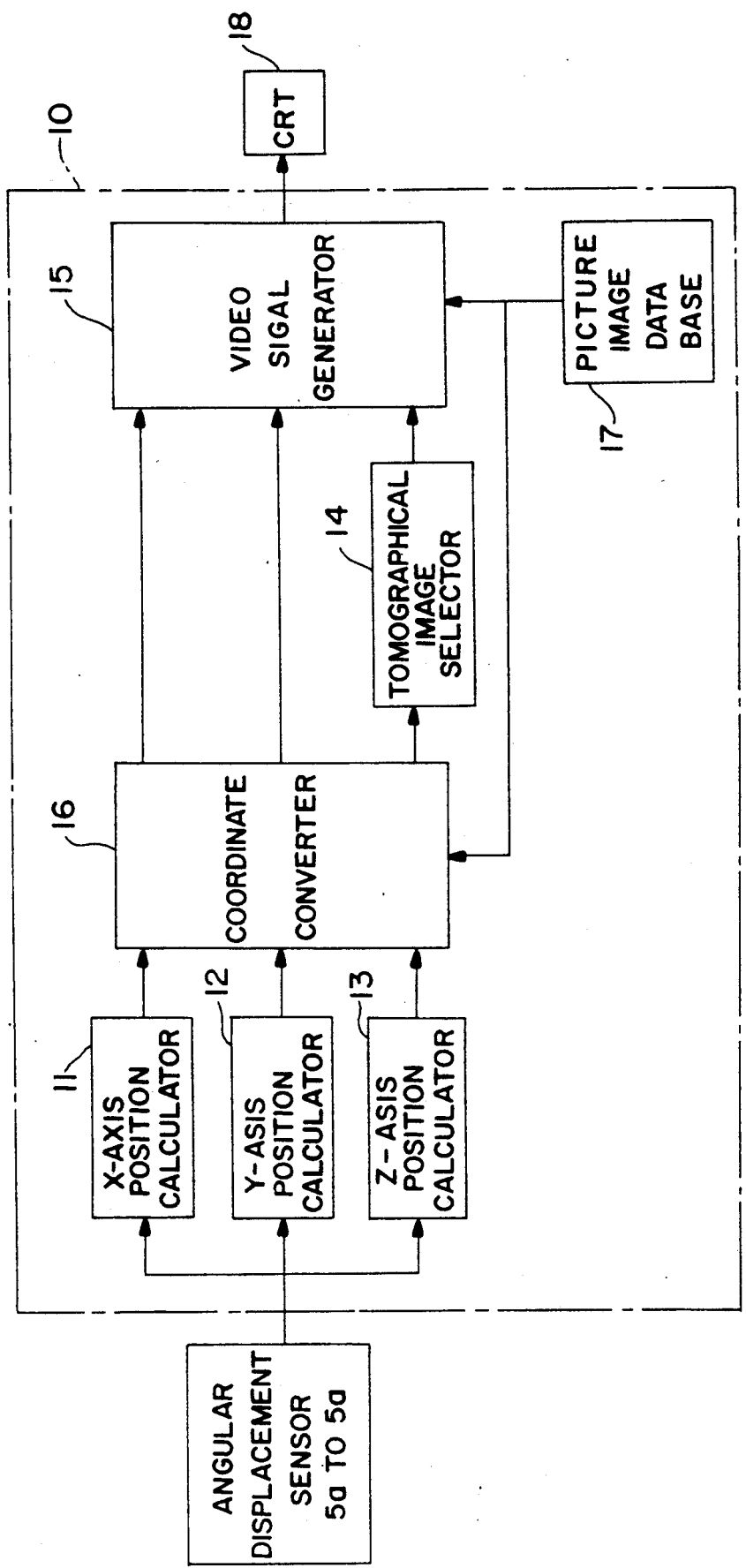
FIG. 3 is a block diagram showing a system according to the present invention.

Referring to FIG. 3 which shows a system of the present invention, the system comprises a microcomputer 10 and a cathode-ray tube (CRT) 18. The microcomputer 10 has an X-axis position calculator 11 for the tip end of the pointer 6, an Y-axis position calculator 12 and a Z-axis position calculator 13, which are supplied with output signals from angular displacement sensors 5a to 5e to produce output signals X, Y, Z, each representing the position along the axis.

Figure 4:
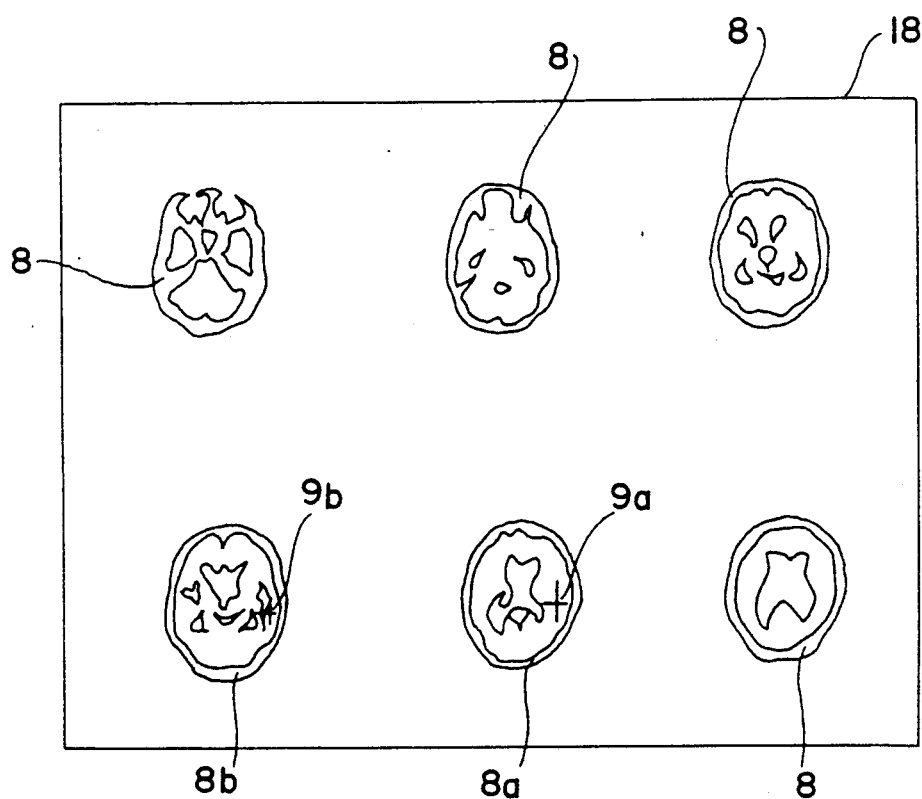
FIG. 4 is an illustration of CT images displayed on a cathode-ray tube.

Thus, the position of the tip end of the pointer 6 with respect to the arm-base coordinate is determined. The microcomputer further comprises a coordinate converter 16 for converting the arm-base coordinate system to a coordinate of a tomographical image coordinate system, a tomographical image selector 14, which is applied with the output signal Z representing the height of the pointer tip, a video signal generator 15, and a picture image data base 17. The CRT 18 displays six CT images 8 of a patient's head as shown in FIG. 4.

An origin is set on the surface of the patient's head, for example on the nasion of the head. In the coordinate converter 16, a coordinate with respect to the CT image 6 on the CRT 18, based on the origin is stored. The computer is structured so that when the articulated arm S is manipulated and the pointer tip contacts the nasion and other predetermined positions, for example the top of the head, and right and left ears, positions of these points with respect to the arm-base coordinate are received in the coordinate converter 16.

Thus, output signals X, Y, Z of the calculator 11, 12, 13 are converted to signals X', Y', Z' on the CT image to coordinate. In accordance with the signals X' and Y' and the output of the selector 14, the generator 15 produces a video signal with reference to informations from the picture image data base 17. The position of the pointer tip is displayed by a cross-mark 9a by the crossmarker on a selected CT images as shown in FIG. 4.

The system can be used as follows. Before an incision on the scalp of the patient, the position of the affected part is searched from the outside of the scalp in a following manner. When the tip of pointer 6 is touched the surface of the patient's head, the position of the tip is indicated by the cross-mark 9a on the CRT 18. The holder 3 of arm S is positioned so the mark is located at a position near the affected part. After that, the holder 3 is pushed toward the scalp near the affected part, the pointer 6 is retracts into the holder. In accordance with the movement of the holder, the cross-mark enters into the selected CT image, thereby indicating the affected part. Thus, the optimum approach to the affected part is designated on the patient's scalp, and an incision is made about the designated position.

The pointer 6 is secured to the holder 3 by the nut 7. During the surgery, the pointer 6 can be inserted into the brain, so that the position of the pointer tip is displayed by the cross-marker 9a. The marker 9a on a CT image 8a having a larger size than a marker 9b on a CT image 8b means that the pointer 6 is located at a position adjacent the CT image 8a nearer than the CT image 8b. Thus, it is possible to locate the pointer tip adjacent the affected part, thereby indicating the depth of the tip, that is the affected part by the notches 6a on the pointer. Thereafter, the pointer is removed from the patient's head, and the surgery on the affected part is performed by surgeons.

Since the exact position to be operated is sensed by the system, the surgery can be exactly performed.

While the invention has been described in conjunction with preferred specific embodiments thereof, it will be understood that this description is intended to illustrate and not limit the scope of the invention, which is defined by the following claims.

What is claimed is:

1. A system for indicating a position in a patient's body where an operation is to be performed, comprising:
    an articulated arm including a base and a plurality of arms, one of said plurality of arms being a foremost arm; said plurality of arms and base being connected to each other by a joint whereby said plurality of arms are adapted to move and are connected by joints;
    a pointer having a tip connected to the end of the foremost arm for pointing at surgical positions;
    angular displacement sensing means provided at each of the joints, for producing angular signals representing an angular displacement of an adjacent arm;
    a cathode-ray tube display for displaying a plurality of tomographic images of a patient's body combined with coordinates associated with the tomographic images;
    calculator means for responding to the angular signals and for producing arm position signals representing the position of the pointer, with respect to arm-base coordinates;
    coordinate conversion means for converting the arm position signals, based on the arm-base coordinates, to tomographic position signals corresponding to the tomographic images on the cathode-ray tube display with respect to CT coordinates;
    means, responsive to the tomographic position signals, and the position of said tip for producing a mark video signal;
    display means responsive to said mark video signal for displaying the position of the tip of the pointer on the cathode-ray tube display as a mark superimposing on the tomographic images developed on the cathode-ray tube display.

2. The system according to claim 1 wherein the pointer is telescopically retractable.

3. The system according to claim 2 further comprising shifting means provided to respond to the distance of advance (retraction) of the foremost arm for shifting the mark on the cathode-ray tube display into the tomographic images in accordance with the distance.

4. The system according to claim 1 wherein the arm position signals comprise an X-axis position signal, Y-axis position signal and Z-axis position signal.

5. The system according to claim 1 further including means for securing the pointer to the foremost arm.

6. The system of claim 1 wherein there are means for securing the pointer to a holder so that the pointer can be universally moved.

7. The system of claim 1 wherein the pointer has a plurality of notches for serving as calibration and holding means.

8. A method for indicating a position in a patient's body where an operation is to be performed using an articulated arm having a plurality of arms including a base, and a foremost arm, the method comprising:
    (a) developing tomographic images of the patient's body including an affected part;
    (b) touching a pointer at the end of the foremost arm to the patient's body;
    (c) obtaining the position of a tip of the pointer, with respect to known arm-base coordinates;
    (d) displaying the tomographic images on a display; and
    (e) displaying the position of the tip of the pointer on the display with a mark and superimposing the mark on the tomographic images on the display.

9. The method of claim 8 wherein the displaying the tomographic images on a display includes using a cathode-ray tube for the display.

* * * * *